(12) United States Patent
Taylor et al.

(10) Patent No.: US 7,758,603 B2
(45) Date of Patent: *Jul. 20, 2010

(54) BLUNT TIP OBTURATOR

(75) Inventors: Scott Taylor, Mission Viejo, CA (US); Matthew A. Wixey, Dana Point, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 752 days.

This patent is subject to a terminal disclaimer.

(21) Appl. No.: 10/514,313

(22) PCT Filed: May 13, 2003

(86) PCT No.: PCT/US03/14924

§ 371 (c)(1), (2), (4) Date: Nov. 12, 2004

(87) PCT Pub. No.: WO03/096879

PCT Pub. Date: Nov. 27, 2003

(65) Prior Publication Data

US 2005/0251191 A1    Nov. 10, 2005

Related U.S. Application Data

(60) Provisional application No. 60/381,469, filed on May 16, 2002.

(51) Int. Cl.
*A61B 17/34* (2006.01)

(52) U.S. Cl. ............... 606/185; 606/108; 604/164.01; 604/264

(58) Field of Classification Search ............ 606/64–67, 606/73, 167, 184, 185, 190–198, 213, 232; 411/409, 387.1–387.8; 604/164.01–164.09, 604/164.1, 164.11–164.13, 165.03, 264, 604/506; 407/54–63
See application file for complete search history.

(56) References Cited

U.S. PATENT DOCUMENTS 1,727,495 A    9/1929    Wappler (Continued)

FOREIGN PATENT DOCUMENTS

DE    41 33 073 A1    4/1992

(Continued)

OTHER PUBLICATIONS

Co-Pending U.S. Appl. No. 10/489,403, filed Mar. 11, 2004; Title: Bladeless Obturator.
Co-Pending U.S. Appl. No. 10/956,167, filed Oct. 3, 2003; Title: Bladeless Optical Obturator.
Co-Pending U.S. Appl. No. 11/170,567, filed Jun. 29, 2005; Title: Insufflating Optical Surgical Instrument.

(Continued)

*Primary Examiner*—Anhtuan T Nguyen
*Assistant Examiner*—Kathleen Sonnett
(74) *Attorney, Agent, or Firm*—Pui Tong Ho; Patrick Y. Ikehara; David G. Majdali

(57) ABSTRACT

A surgical obturator comprising an elongate shaft extending along an axis between a proximal end and a distal end, and a bladeless tip disposed at the distal end of the shaft having a conical surface forming proximally into an outer surface, the outer surface extending distally to a blunt point and having a pair of side sections. The side sections extend from the blunt point radially outwardly with progressive positions proximally along the axis. The conical surface facilitates insertion of the obturator with a reduced penetration force and minimizes tenting of the body wall. The conical surface further facilitates separation of different layers of the body wall and provides proper alignment of the tip between the layers. The surgical obturator may be constructed from a disposable or reusable material such as a metal or an autoclavable polymer.

10 Claims, 6 Drawing Sheets

U.S. PATENT DOCUMENTS

| | | | |
|---|---|---|---|
| 2,102,274 A | 12/1937 | Larimore | |
| 2,764,148 A | 9/1956 | Sheldon | |
| 2,764,149 A | 9/1956 | Sheldon | |
| 2,877,368 A | 3/1959 | Sheldon | |
| 3,021,834 A | 2/1962 | Sheldon | |
| 3,042,022 A | 7/1962 | Sheldon | |
| 3,417,745 A | 12/1968 | Sheldon | |
| 3,817,251 A | 6/1974 | Hasson | |
| 3,994,287 A | 11/1976 | Turp et al. | |
| 4,168,882 A | 9/1979 | Hopkins | |
| 4,191,191 A | 3/1980 | Auburn | |
| 4,254,762 A | 3/1981 | Yoon | |
| 4,414,966 A * | 11/1983 | Stednitz | 606/73 |
| 4,535,773 A | 8/1985 | Yoon | |
| 4,813,400 A | 3/1989 | Washizuka et al. | |
| 5,104,316 A * | 4/1992 | McSpadden | 433/102 |
| 5,217,441 A | 6/1993 | Shichman | |
| 5,258,003 A * | 11/1993 | Ciaglia et al. | 606/185 |
| 5,271,380 A | 12/1993 | Riek et al. | |
| 5,279,567 A | 1/1994 | Ciaglia et al. | |
| 5,342,382 A | 8/1994 | Brinkerhoff et al. | |
| 5,431,151 A | 7/1995 | Riek et al. | |
| 5,441,041 A | 8/1995 | Sauer et al. | |
| 5,569,292 A | 10/1996 | Scwemberger et al. | |
| 5,609,604 A * | 3/1997 | Schwemberger et al. | 606/185 |
| 5,662,673 A | 9/1997 | Kieturakis | |
| 5,676,611 A | 10/1997 | Foster | |
| 5,697,947 A * | 12/1997 | Wolf et al. | 606/185 |
| 5,720,761 A | 2/1998 | Kaali | |
| 5,792,112 A | 8/1998 | Hart et al. | |
| 5,797,944 A | 8/1998 | Nobles et al. | |
| 5,817,061 A | 10/1998 | Goodwin | |
| 5,836,957 A | 11/1998 | Shulz | |
| 5,893,865 A | 4/1999 | Swindle et al. | |
| 6,019,776 A * | 2/2000 | Preissman et al. | 606/185 |
| 6,077,481 A | 6/2000 | Ichida et al. | |
| 6,203,559 B1 * | 3/2001 | Davis et al. | 606/198 |
| 6,478,806 B2 * | 11/2002 | McFarlane | 606/185 |
| 6,508,759 B1 | 1/2003 | Taylor et al. | |
| 2002/0013597 A1 | 1/2002 | McFarlane | |
| 2002/0133188 A1 * | 9/2002 | O'Heeron et al. | 606/185 |
| 2002/0183775 A1 * | 12/2002 | Tsonton et al. | 606/185 |
| 2003/0059263 A1 * | 3/2003 | Chen | 407/54 |
| 2005/0065543 A1 * | 3/2005 | Kahle et al. | 606/190 |
| 2005/0107816 A1 * | 5/2005 | Pingleton et al. | 606/185 |
| 2005/0149096 A1 * | 7/2005 | Hilal et al. | 606/191 |

FOREIGN PATENT DOCUMENTS

| | | |
|---|---|---|
| WO | WO 96/10361 | 4/1996 |
| WO | WO 00/54648 | 9/2000 |
| WO | WO 02/01998 A2 | 1/2002 |
| WO | WO 03/026512 | 4/2003 |
| WO | WO 03/026512 A1 | 4/2003 |
| WO | WO 03/096879 A2 | 11/2003 |
| WO | WO 03/096879 A3 | 11/2003 |
| WO | WO 2005/063134 A1 | 7/2005 |

OTHER PUBLICATIONS

U.S. Appl. No. 10/745,262, filed Dec. 23, 2003; Title: Catheter With Conduit Traversing Tip.

Co-Pending U.S. Appl. No. 11/868,883, filed Oct. 8, 2007; Title: Visual Insufflation Port.

Taut, Inc., ADAPT—Asymmetrical Dilating Access Port, Geneva Illinois.

Karl Storz, The Karl Storz Ternamian EndoTIP (TM) System, date: Aug. 27, 2001.

Karl Storz, Zerocart Trocar with eccentric tip, Recklinghausen, Germany, date: Mar. 7, 2001.

Ethicon Endo-Surgery, Inc., Endopath Minimally Invasive Access, date: 2000.

* cited by examiner

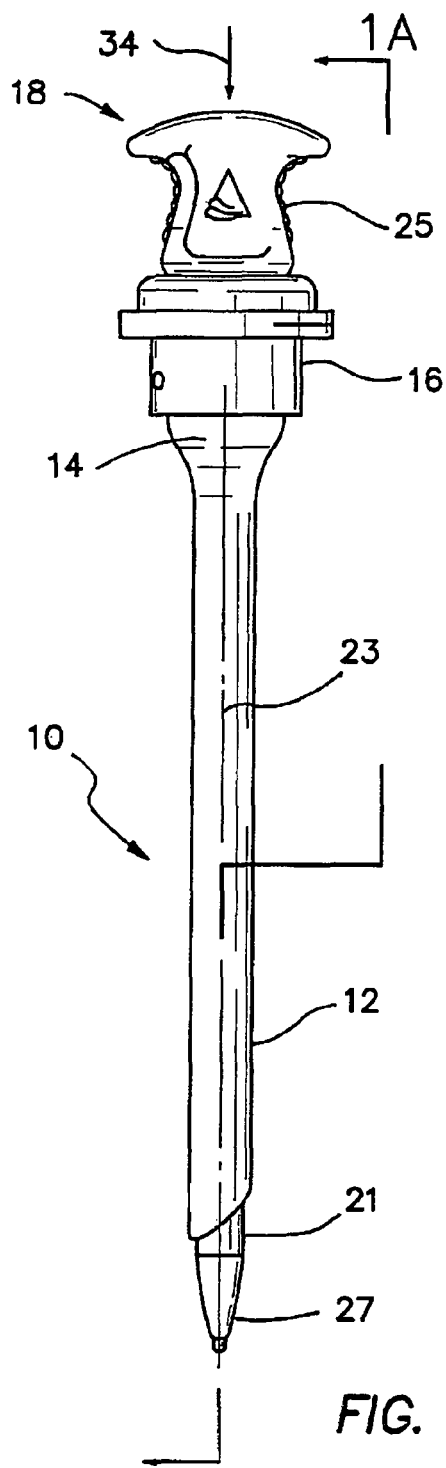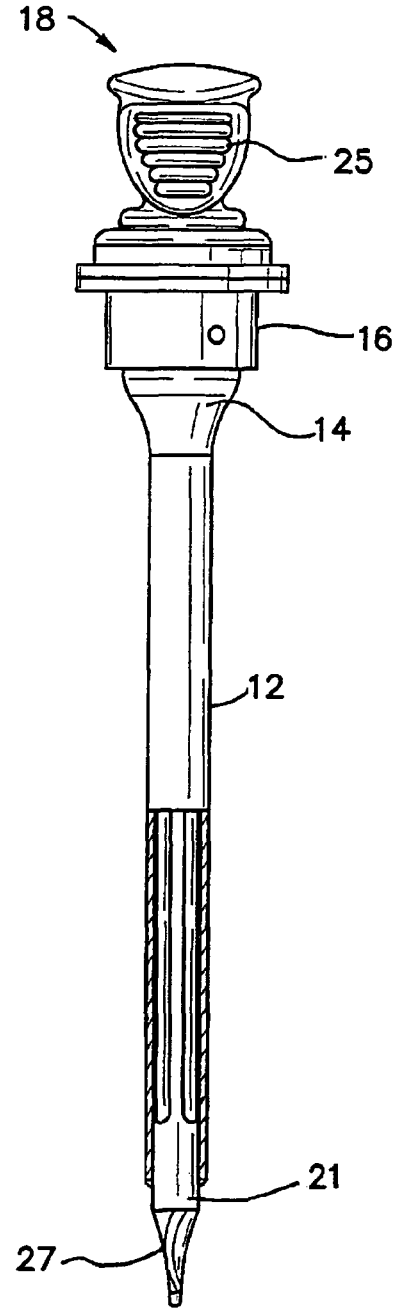
FIG. 1
FIG. 1A

BLUNT TIP OBTURATOR

This is a non-provisional application claiming priority to provisional application Ser. No. 60/381,469, filed May 16, 2002, entitled "Cone Tip Obturator," and incorporating by reference the same provisional application and international application No. PCT/US02/06759, filed Mar. 4, 2002, entitled "Bladeless Obturator."

BACKGROUND OF THE INVENTION

1. Field of the Invention

This invention generally relates to trocar systems including obturators and, more specifically, to blunt cone tip obturators.

2. Discussion of the Prior Art

Trocar systems have been of particular advantage in facilitating less invasive surgery across a body wall and within a body cavity. This is particularly true in the case of the abdominal surgery where trocars have provided working channels across the abdominal wall to facilitate the use of instruments within the abdominal cavity.

The trocar systems of the past typically include a cannula, which defines the working channel, and an obturator which is used to place the cannula across the abdominal wall. The obturator is inserted into the working channel of the cannula and then pushed through the abdominal wall with a penetration force of sufficient magnitude to result in penetration of the abdominal wall. Once the cannula is in place, the obturator can be removed.

In the past, obturators have been developed with an intent to provide a reduction in the force required for penetration. Sharp blades have typically been used to enable the obturator to cut its way through the abdominal wall. While the blades have facilitated a reduced penetration force, they have been of particular concern once the abdominal wall has been penetrated. Within the abdominal cavity, there are organs which need to be protected against any puncture by an obturator.

In some cases, shields have been provided with the obturators in order to sense penetration of the abdominal wall and immediately shield the sharp blades. These shielding systems have been very complex, have required a large amount of time to deploy, and have generally been ineffective in protecting the organs against the sharp blades.

Blunt-tip obturators have been contemplated with both symmetrical and asymmetrical designs. While the blunt tip tends to inhibit damage to interior organs, it also tends to increase the penetration force associated with the obturator. Thus, there is a need in the art for an improved bladeless obturator that reduces the force required to place the obturator across the abdominal wall.

SUMMARY OF THE INVENTION

In accordance with the present invention, a blunt tip obturator similar to that described in international application No. PCT/US02/06759 further including a cone at its distal tip is disclosed with characteristics that reduce the force required to penetrate the abdominal wall. The addition of the cone also reduces the tendency for the abdominal wall and the peritoneum to deflect or "tent" during insertion of the obturator. The blunt cone tip obturator of the invention penetrates and twists radially from a distal end to a proximal end of the tip. The blunt cone tip obturator facilitates insertion with a reduced penetration force as the user moves the tip back and forth radially while applying an axial penetration force. The blunt cone tip obturator can be directed and inserted between the fibers and then rotated to provide increased penetration and fiber separation.

These and other features and advantages of the invention will become more apparent with a discussion of preferred embodiments in reference to the associated drawings.

DESCRIPTION OF THE DRAWINGS

FIG. 1 illustrates side views of a trocar system including a cannula with associated valve housing, and an obturator with a blunt cone tip extending through the working channel of the cannula to facilitate placement across the abdominal wall;

DESCRIPTION OF PREFERRED EMBODIMENTS AND BEST MODE OF THE INVENTION

Figure 2:
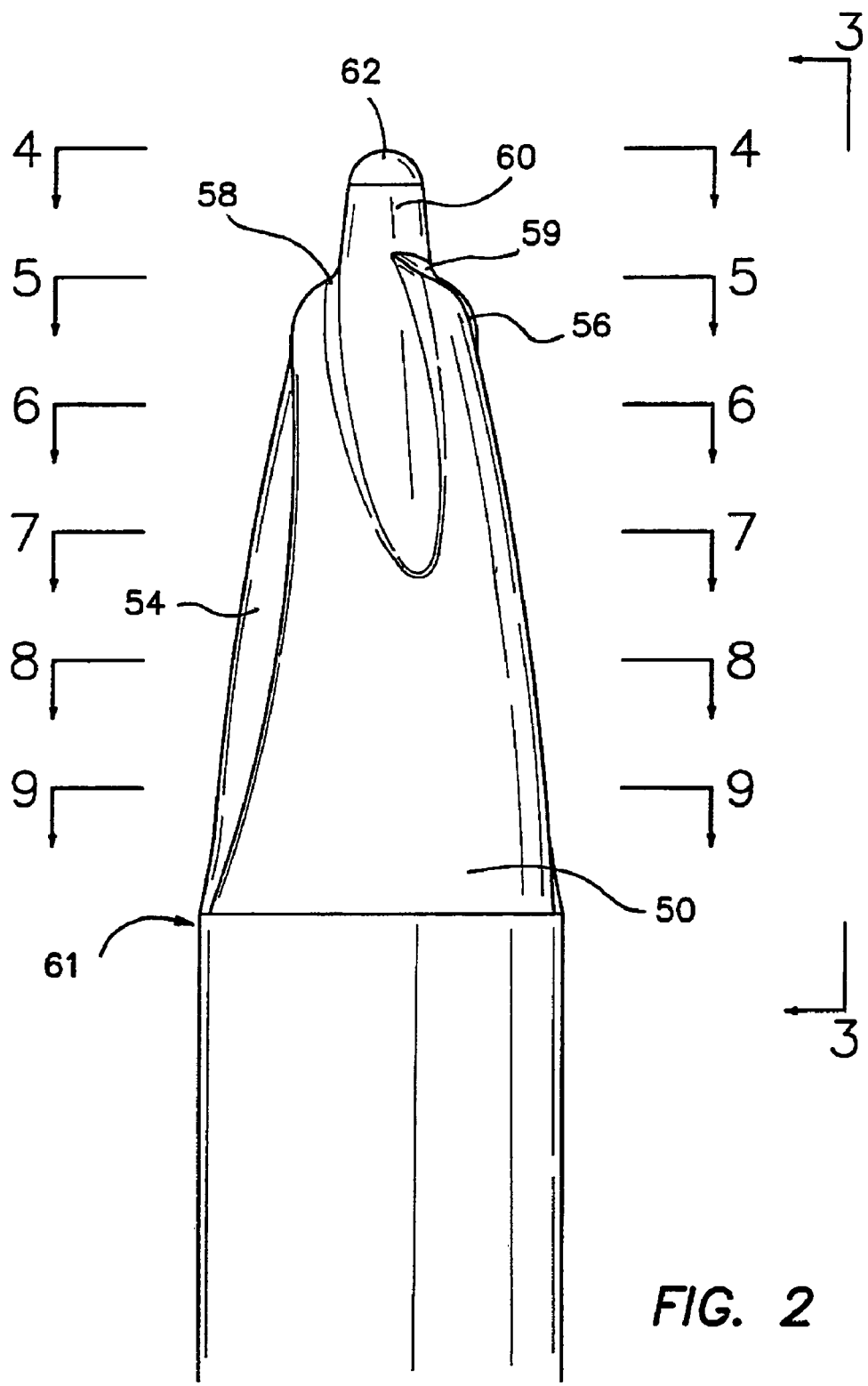
FIG. 2 is a side elevation view of the blunt cone tip of a preferred embodiment of the invention.

A trocar system is illustrated in FIG. 1 and is designated by reference numeral 10. This system includes a cannula 12, defining a working channel 14, and a valve housing 16. The system 10 also includes an obturator 18 having a shaft 21 extending along an axis 23. A handle 25 is disposed at a proximal end of the shaft at 21 while a blunt cone tip 27 is disposed at a distal end of the shaft 21. The shaft 21 of the obturator 18 is sized and configured for disposition within the working channel 14 of the cannula 12. With this disposition, the obturator 18 can be directed to penetrate a body wall such as the abdominal wall to provide the cannula 12 with access across the wall and into a body cavity, such as the peritoneal or abdominal cavity. The blunt cone tip 27 serves to direct the obturator 18 through the abdominal wall and the peritoneum, and can be removed with the obturator 18 once the cannula 12 is operatively disposed with the working channel 14 extending into the abdominal cavity.

In order to facilitate penetration of the abdominal wall by the trocar system 10, a penetration force, represented by an arrow 34, is typically applied along the axis 23. It can be appreciated that the force required to penetrate the abdominal wall drops significantly once the wall is penetrated. Further application of the force 34, even for an instant of time, can result in injury to organs within the cavity. Where the obturators of the past have included blades facilitating penetration of the abdominal wall, these blades have been particularly threatening and detrimental to the interior organs.

Consequently, in accordance with the present invention, the tip 27 is provided with a blunt cone configuration. Blunt tips have been used in the past to reduce any potential for damage to interior organs. However, these blunt tips have increased the amount of force 34 required for penetration of the abdominal wall. The blunt cone tip 27 of the present invention takes into account the anatomical configuration of the abdominal wall with an improved structural design and method of insertion.

To fully appreciate these aspects of this invention, it is helpful to initially discuss the anatomy associated with the abdominal wall. The abdominal wall typically includes a skin layer and a series of muscle layers. The muscle layers are each defined by muscle fibers that extend generally parallel to each other in a direction that is different for each of the layers. For example, fibers of a first muscle layer and a second muscle layer may extend in directions that are 45 degrees off of each other.

Having noted the directional nature of the muscle fibers, it can be appreciated that such a structure is most easily penetrated by an obturator having a blunt cone tip. The blunt cone tip also has a rectangular and twisted configuration so as to provide better movement between the muscle layers. That is, the blunt cone tip is capable of being moved generally parallel to and between the fibers associated with a particular muscle layer. As a result, the obturator of the present invention reduces the penetration force 34 required to push the obturator 18 through a particular layer.

As described earlier, the fibers of the muscle layers may be oriented at different angles to each other such that proper alignment of the tip 27 for penetration of one layer may not necessarily result in proper alignment for penetration of the next layer. For at least this reason, the obturator 18 has a blunt cone tip 27 to direct the obturator 18 through the different layers and a rectangular configuration that is twisted slightly so that penetration of a first layer begins to rotate the distal end of the blunt cone tip 27 into proper orientation for penetration of the next layer.

The twisted configuration of the blunt cone tip 27 also causes the blunt cone tip 27 to function with the mechanical advantage of a screw thread. With this configuration, a preferred method of placement requires that the user grip the handle 25 of the obturator 18 and twist it about the axis 23. This twisting motion in combination with the screw configuration of the blunt cone tip 27 converts radial movement into forward movement along the axis 23. Thus, the user applies both a forwardly directed force as well as a radial force to move the trocar system 10 in a forward direction. Since all of the force supplied by the user is not directed axially along the arrow 34, this concept avoids the tendency of prior trocar systems to jump forward upon penetration of the abdominal wall.

Figure 3:
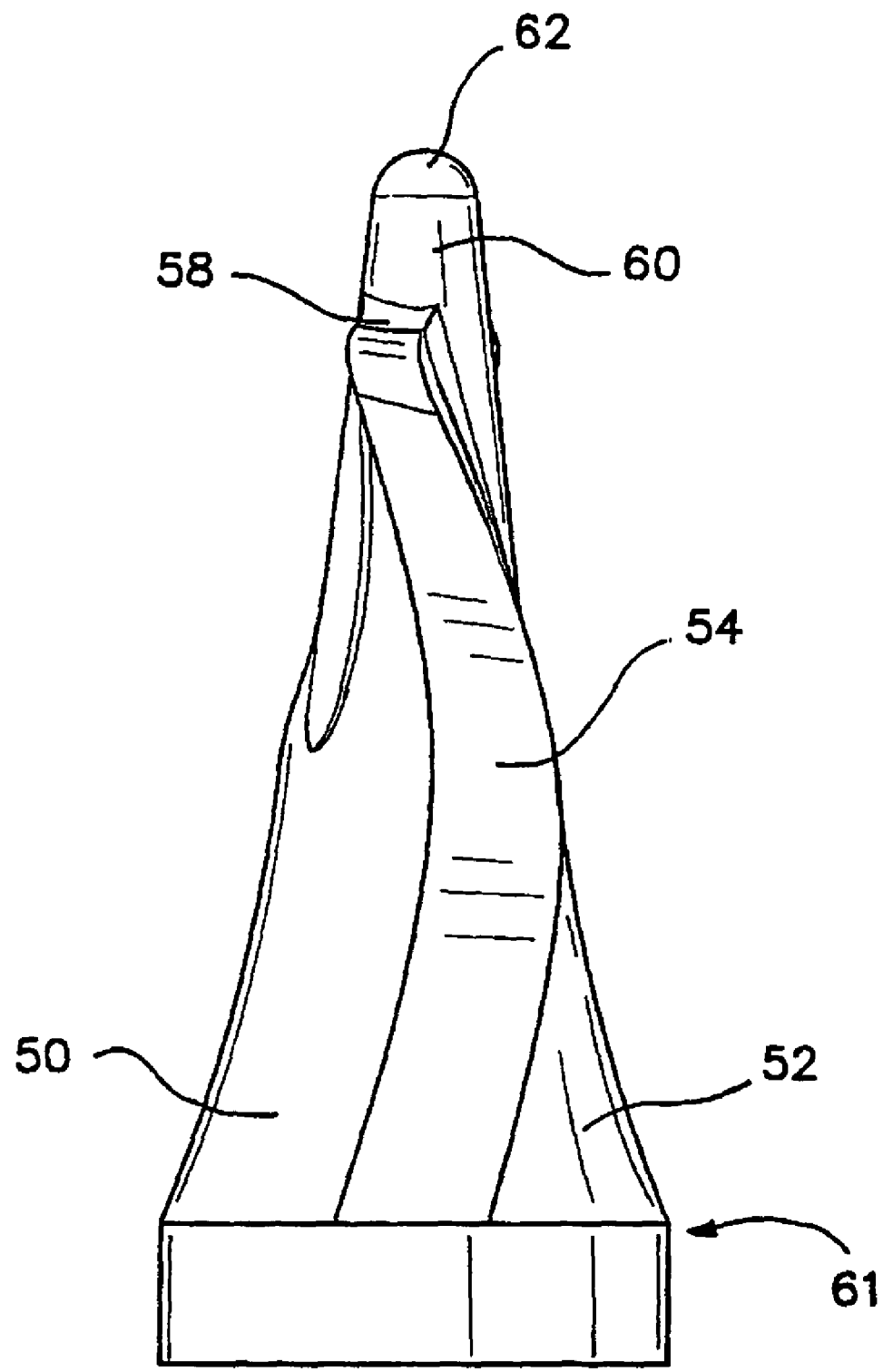
FIG. 3 is a side elevation view of the blunt cone tip taken along line 3-3 of FIG. 2.

The twisted configuration of the blunt cone tip 27 is most apparent in the side elevation views of FIGS. 2 and 3. In this embodiment, the blunt cone tip 27 comprises generally of eight surfaces: two opposing surfaces 50 and 52, separated by two side surfaces 54 and 56, two end surfaces 58 and 59, a conical surface 60 formed in surfaces 50 and 52 around axis 23 and extending beyond end surfaces 58 and 59, and a blunt surface 62. A plane drawn through the axis 23 would show the tip 27 to be composed of two symmetrical halves.

Figure 4:
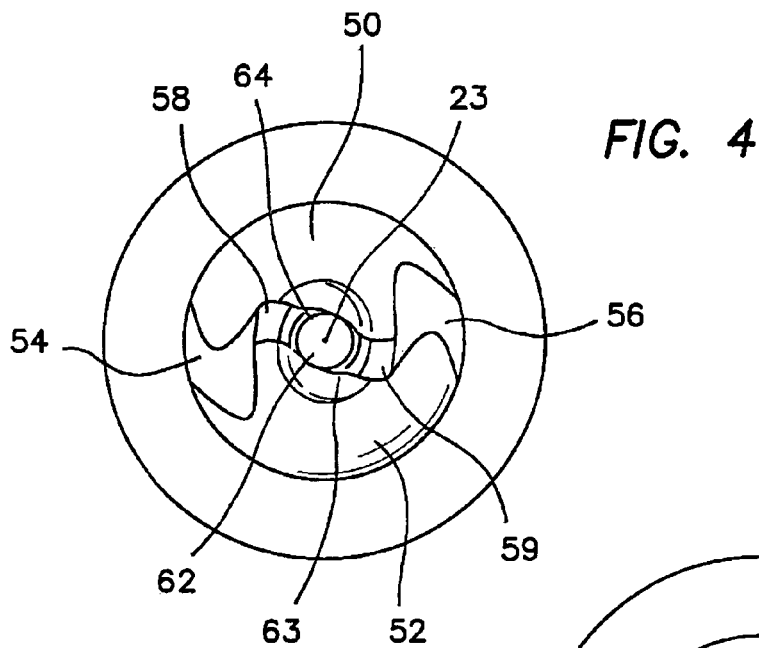
FIG. 4 is an end view taken along line 4-4 of FIG. 2.

The surfaces 50 and 52, side surfaces 54 and 56, and conical surface 60 generally define the cross section of the blunt cone tip 27 from blunt surface 62 to proximal end 61. This configuration can best be appreciated with reference to the cross section views of FIGS. 4-9. In FIG. 4, the distal end of the blunt cone tip 27 is shown with a circle 64 having the smallest circular area and a rectangle 63 having the greatest length-to-width ratio. The rectangle 63 has a twisted, S-shaped configuration at end surfaces 58 and 59.

As views are taken along progressive proximal cross sections, it can be seen that the circle 64 becomes larger and the rectangle 63 becomes less twisted, and the width increases relative to the length of the rectangle 63. The spiral nature of the blunt cone tip 27 is also apparent as the circle 64 and rectangle 63 move counterclockwise around the axis 23. This is perhaps best appreciated in a comparison of the circle 64 and the rectangle 63 in FIG. 6 relative to that in FIG. 5. With progressive proximal positions, the circle 64 begins to expand with increasing circular area and the rectangle 63 begins to widen with a reduction in the ratio of length to width. The long sides of the rectangle 63 also tend to become more arcuate as they approach a more rounded configuration most apparent in FIGS. 8 and 9. That is, the circle 64 and the rounded rectangle 63 remain concentric and the rounded rectangle becomes more rounded with progressive proximal positions. Furthermore, the circle 64 expands at a lesser rate than the rectangle 63, which eventually absorbs the circle 64 as shown in FIGS. 8 and 9. In these figures, it will also be apparent that the rotation of the rectangle 63 reaches a most counterclockwise position and then begins to move clockwise. This is best illustrated in FIGS. 7-9. This back and forth rotation results from the configuration of the side surfaces 54 and 56, which in general are U-shaped as best illustrated in FIGS. 2 and 3

The ratio of the length to width of the rectangle 63 is dependent on the configuration of the side surfaces 54 and 56, which define the short sides of the rectangle 63 as well as the configuration of the surfaces 50 and 52, which define the long sides of the rectangle 63. Again with reference to FIGS. 2 and 3, it can be seen that the side surfaces 54 and 56 are most narrow at the end surfaces 58 and 59. As the side surfaces 54 and 56 extend proximally, they reach a maximum width near the point of the most counterclockwise rotation, shown generally in FIG. 8, and then reduce in width as they approach the proximal end 61. Along this same distal to proximal path, the surfaces 50 and 52 transition from a generally flat configuration at the end surfaces 58 and 59 to a generally rounded configuration at the proximal end 61.

Figure 5:
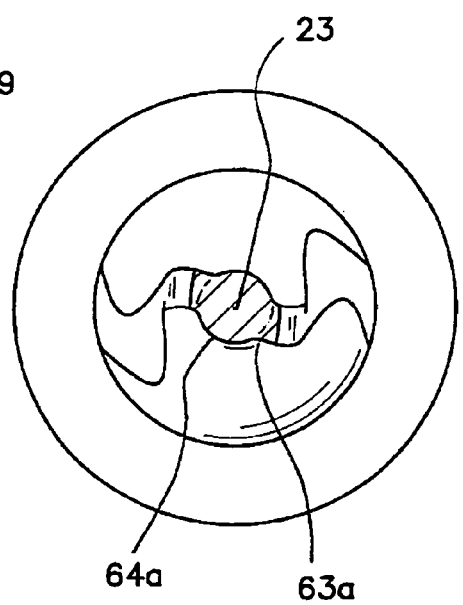
FIG. 5 is a radial cross-section view taken along line 5-5 of FIG. 2.
Figure 6:
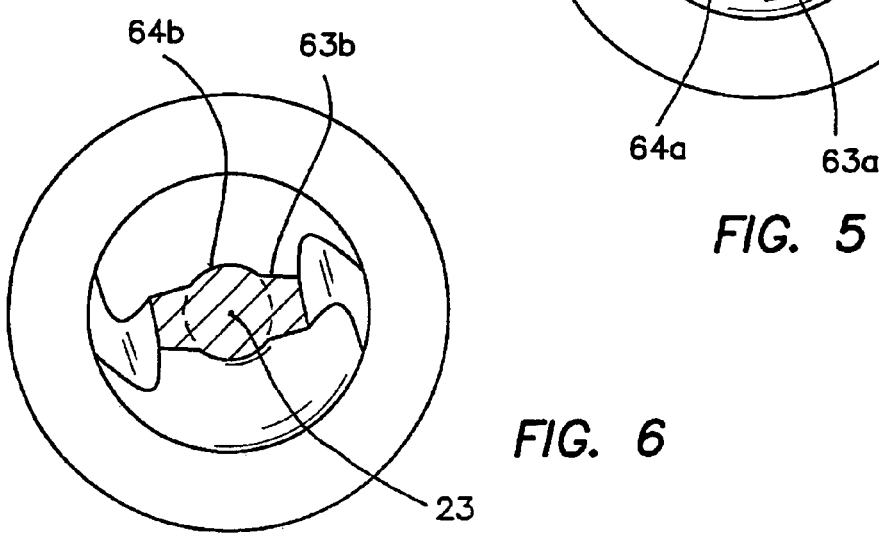
FIG. 6 is a radial cross-section view taken along line 6-6 of FIG. 2.
Figure 7:
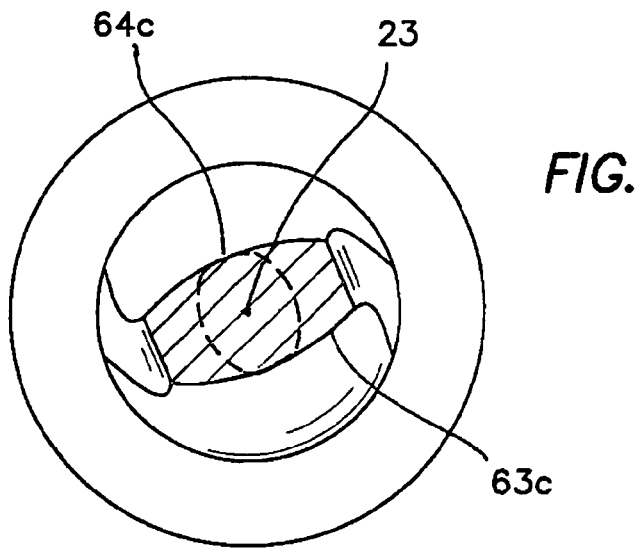
FIG. 7 is a radial cross-section view taken along line 7-7 of FIG. 2.
Figure 8:
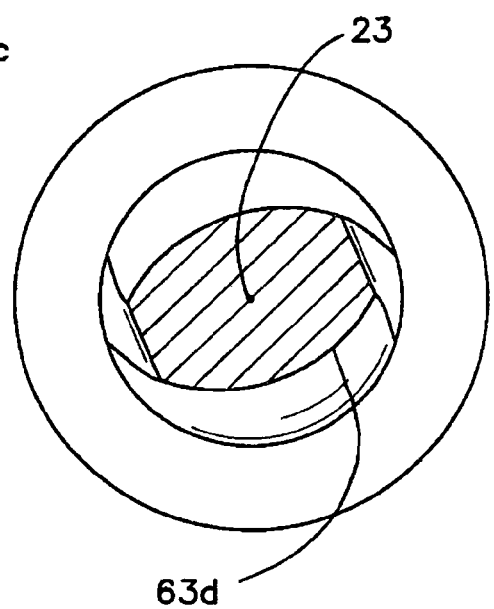
FIG. 8 is a radial cross-section view taken along line 8-8 of FIG. 2.
Figure 9:
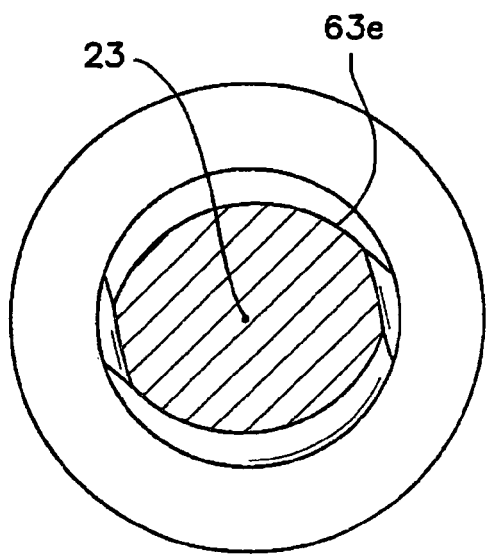
FIG. 9 is a radial cross-section view taken along line 9-9 of FIG. 2.
Figure 10:
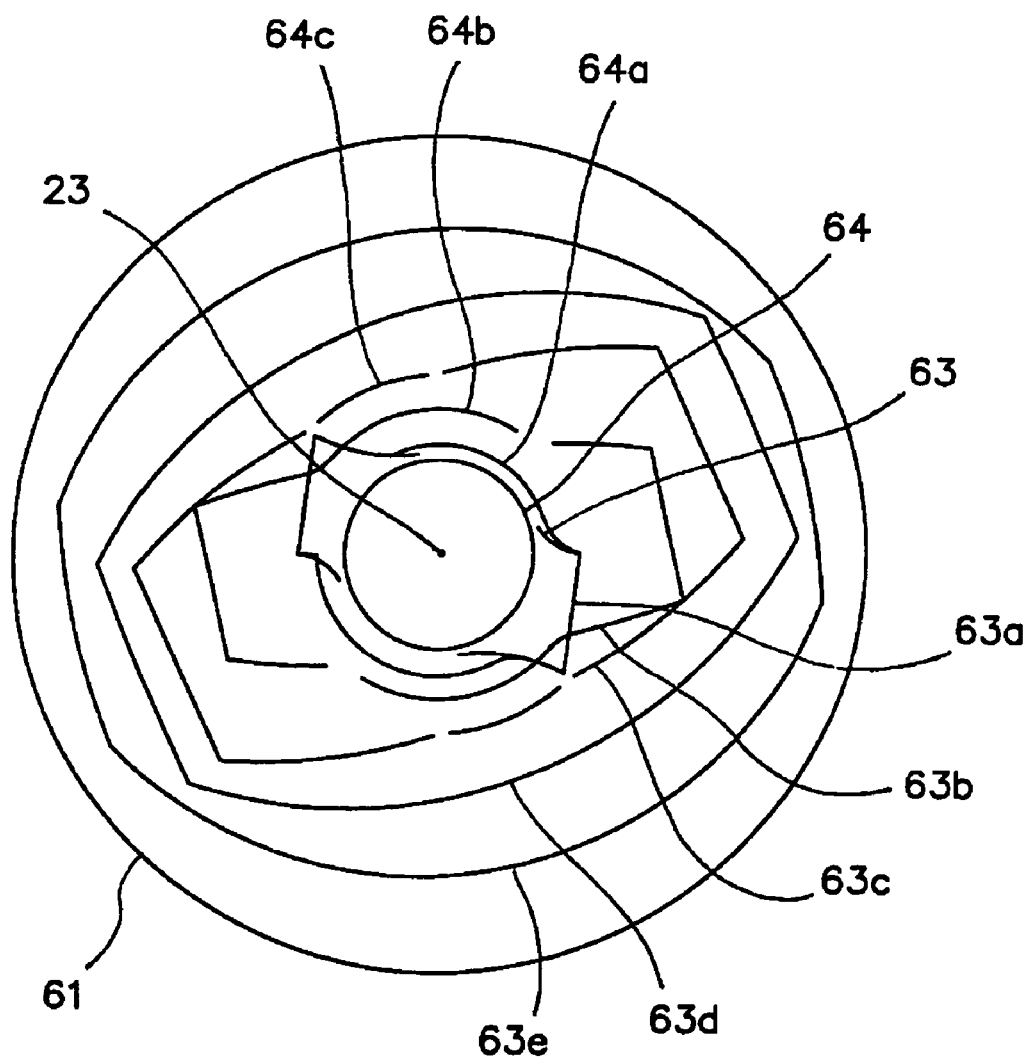
FIG. 10 is a schematic view illustrating each of the FIGS. 4-9 super-imposed to facilitate an understanding of the blunt cone tip and its twisted configuration.

In the progressive views of FIGS. 5-7, the circle 64 is further designated with a lower case letter a, b or c, respectively; similarly, the rectangle 63 is further designated with a lower case letter a, b, c, d or e, respectively, in FIGS. 5-9. In FIG. 10, the circles 64, 64a-64c and the rectangles 63, 63a-63e are superimposed on the axis 23 to show their relative sizes, shapes and angular orientations.

A preferred method of operating the trocar system 10 benefits significantly from this preferred shape of the blunt cone tip 27. With a conical configuration at the distal point and a rectangular configuration at a distal portion of the tip, the tip 27 appears much like a flathead screwdriver having a cone at its tip. Specifically, the blunt tip includes a conical structure extending outward from the end surfaces 58 and 59 that serves to direct the obturator through the abdominal wall and peritoneum The cone tip has a radius of approximately 0.025". The incorporation of the cone onto the rectangular configuration reduces the insertion force required to traverse the abdominal wall. An advantage of the obturator of the invention is it provides a safer and more controlled entry of the abdominal cavity.

It is preferable that the lengths of the end surfaces 58 and 59 are aligned parallel with the fibers of each muscle layer. With this shape, the blunt cone tip can be used to locate or pinpoint a desired location and penetrate the abdominal wall. A simple back and forth twisting motion of the blunt cone tip tends to separate the fibers along natural lines of separation, opening the muscle layer to accept the larger diameter of the cannula 12. By the time the first layer is substantially penetrated, the conical and twisted configuration of the blunt cone tip 27 directs and turns the rectangle 63 more into a parallel alignment with fibers in the next layer. Again, the blunt cone tip facilitates penetration, and the twisting or dithering motion facilitates an easy separation of the fibers requiring a significantly reduced penetration and insertion force along the arrow 34.

It should be further noted that the blunt cone tip 27 is bladeless and atraumatic to organs and bowel within the peritoneal or abdominal cavity. The blunt cone tip 27 also minimizes tenting of the peritoneum and allows for a safe entry. The device is typically used in conjunction with the cannula 12 to create an initial entryway into the peritoneal cavity. The obturator 18 is first inserted through the valve housing 16 and into the cannula 12. The entire trocar system 10 is then inserted through the abdominal wall and into the peritoneal cavity. Once the cannula 12 is properly placed, the obturator 18 can be removed.

The invention facilitates a unique method of penetrating and separating tissue and could apply to any object with a blunt cone tip and generally flat sides. When inserted into the peritoneum the blunt cone tip requires very little area to move safely between tissue and muscle fibers. The device can then be rotated in alternating clockwise and counterclockwise directions while the downward penetration force is applied. When rotated in alternating directions, the tissue is moved apart and a larger opening is created for a profile of greater cross sectional area to follow. This process continues with safety as the device enters the peritoneal cavity and moves to its operative position.

When the cannula 12 is ultimately removed, the size of the opening left in the tissue is minimal. Importantly, this opening is left sealed due to a dilating effect caused by the mere separation of fibers. Since there are no blades or sharp edges to cut muscle fiber, the healing process is significantly shortened.

The blunt cone tip 27 of the obturator 18 can be fabricated of a translucent or clear material, and the handle 25 can be provided with a passageway along the inside of the tip. With this configuration, a laparoscope can be inserted through the handle of the obturator and through the shaft to the tip. Insertion can then be monitored through the laparoscope and the clear tip of the obturator, in order to further ensure safe entry.

The obturator 18 can be constructed as a single component or divided into multiple components such as the shaft 21 and the blunt cone tip 27. If the obturator 18 is constructed as a single component, it may be constructed of either disposable or reusable materials. If the obturator 18 is constructed as two or more components, each component can be made either disposable or reusable as desired for a particular configuration. In a preferred embodiment, the obturator is constructed as a single component made from a reusable material such as metal (e.g., stainless steel) or an autoclavable polymer to facilitate re-sterilization.

In another embodiment of the invention, the blunt cone tip 27 can be coated or otherwise constructed from a soft elastomeric material. In such a case, the material could be a solid elastomer or composite elastomer/polymer.

The shaft 21 of the obturator 18 could be partially or fully flexible. With this configuration, the obturator 18 could be inserted through a passageway containing one or more curves of virtually any shape. A partially or fully flexed obturator 18 could then be used with a flexible cannula 12 allowing greater access to an associated body cavity.

The obturator 18 could also be used as an insufflation needle and provided with a passageway and valve to administer carbon dioxide or other insufflation gas to the peritoneal cavity. The obturator 18 could also be used with an insufflation needle cannula, in which case removal of the obturator 18 upon entry would allow for rapid insufflation of the peritoneal cavity.

It will be understood that many modifications can be made to the disclosed embodiments without departing from the spirit and scope of the invention. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments.

The invention claimed is:

1. A surgical obturator adapted to penetrate a body wall, comprising:
   an elongate shaft extending along an axis between a proximal end and a distal end; and
   a non-expanding bladeless tip disposed at the distal end of the shaft having a conical surface forming proximally into an outer surface and extending distally to a blunt point, said outer surface having a pair of side sections separated by an intermediate section,
   wherein the side sections extend from the conical surface radially outwardly with progressive positions proximally along the axis,
   wherein the outer surface in radial cross section has a general configuration of a circle superimposed on a rectangle;
   the intermediate section includes a distal portion in proximity to the blunt point and a proximal portion in proximity to the shaft;
   the distal portion of the intermediate section being twisted in a first radial direction; and
   the proximal portion of the intermediate section being twisted in a second radial direction opposite the first radial direction.

2. The surgical obturator of claim 1, wherein the conical surface facilitates insertion of the obturator with a reduced penetration force and minimizes tenting of the body wall.

3. The surgical obturator of claim 1, wherein the conical surface facilitates separation of different layers of the body wall and provides proper alignment of the tip between the layers.

4. The surgical obturator of claim 1, wherein:
   the side sections include a distal portion in proximity to the blunt point and a proximal portion in proximity to the shaft; and
   the distal portion of the side sections being twisted radially with respect to the proximal portion of the side sections.

5. The surgical obturator of claim 1, wherein the distal portion of the intermediate section has a width which increases proximally.

6. The surgical obturator of claim 1, wherein the conical surface forms into said side sections extending proximally beyond said blunt point.

7. The surgical obturator of claim 1, wherein the circle and the rectangle become more concentric with progressive proximal positions.

8. The surgical obturator of claim 1, wherein along a portion of the outer surface at one or more proximal positions, the circle radial cross section has a diameter larger than a width of short sides of the rectangle radial cross section.

9. The surgical obturator of claim 1, wherein the elongate shaft has a minimum diameter larger than a maximum diameter of the non-expanding bladeless tip.

10. A surgical obturator adapted to penetrate a body wall, comprising:
- an elongate shaft extending along an axis between a proximal end and a distal end; and
- a tip disposed at the distal end of the shaft and having a first outer surface between two side surfaces raised relative to the first outer surface, a second outer surface between the two side surfaces and opposing the first outer surface, the first outer surface, second outer surface and two side surfaces forming a continuous surface extending distally to a truncated conical tip having a hemispherical blunt end;
- wherein the continuous surface in radial cross section has a general configuration of rectangle with arcuate long sides and straight short sides and the truncated conical tip in radial cross section has a general configuration of a circle;
- wherein one of the two side surfaces extends perpendicularly away from the distal end and the axis of the shaft with a distal portion of the one of the two side surfaces twists upwardly transverse to the perpendicular direction and the axis of the shaft and a proximal portion of the one of the two side surfaces twists downwardly opposite of the upwardly twisted distal portion traverse to the perpendicularirection and the axis of the shaft.

* * * * *

UNITED STATES PATENT AND TRADEMARK OFFICE
CERTIFICATE OF CORRECTION

| | | |
|---|---|---|
| PATENT NO. | : 7,758,603 B2 | Page 1 of 1 |
| APPLICATION NO. | : 10/514313 | |
| DATED | : July 20, 2010 | |
| INVENTOR(S) | : Scott V. Taylor and Matthew A. Wixey | |

It is certified that error appears in the above-identified patent and that said Letters Patent is hereby corrected as shown below:

In Column 6, line 62, please delete "become more" and replace with --remain--.

In Column 8, line 13, please delete "perpendicularirection" and replace with --perpendicular direction--.

Signed and Sealed this
Eighteenth Day of October, 2011

David J. Kappos
*Director of the United States Patent and Trademark Office*